United States Patent

Sarver et al.

[11] Patent Number: 5,953,100
[45] Date of Patent: *Sep. 14, 1999

[54] MULTI-CAMERA CORNEAL ANALYSIS SYSTEM

[75] Inventors: Edwin J. Sarver, Merritt Island, Fla.; Henry D'Souza, Cypress, Tex.

[73] Assignee: Eyesys-Premier, Inc., Irvine, Calif.

[ * ] Notice: This patent is subject to a terminal disclaimer.

[21] Appl. No.: 08/956,515

[22] Filed: Oct. 23, 1997

Related U.S. Application Data

[63] Continuation of application No. 08/638,875, Apr. 25, 1996, Pat. No. 5,847,854, which is a continuation of application No. 08/330,979, Oct. 28, 1994, abandoned.

[51] Int. Cl.⁶ ........................................................ A61B 3/14
[52] U.S. Cl. .............................................................. 351/206
[58] Field of Search ................................. 351/205, 206, 351/207, 208, 209, 210, 211, 212, 246; 382/117

[56] References Cited

U.S. PATENT DOCUMENTS

| | | |
|---|---|---|
| 3,169,459 | 2/1965 | Friedberg et al. . |
| 4,372,655 | 2/1983 | Matsumura et al. ..................... 351/211 |
| 4,420,228 | 12/1983 | Humphrey . |
| 4,436,389 | 3/1984 | Sano ........................................ 351/208 |
| 4,597,648 | 7/1986 | Feldon et al. . |
| 4,662,730 | 5/1987 | Outwater et al. . |
| 4,685,140 | 8/1987 | Mount, II . |
| 4,710,003 | 12/1987 | Masuda et al. . |
| 4,859,051 | 8/1989 | Fukuma et al. . |
| 4,863,260 | 9/1989 | Gersten et al. . |
| 4,978,213 | 12/1990 | El Hage . |
| 4,998,819 | 3/1991 | Labinger et al. . |
| 5,016,282 | 5/1991 | Tomono et al. ........................ 382/117 |
| 5,110,200 | 5/1992 | Snook et al. . |
| 5,212,506 | 5/1993 | Yoshimatsu et al. . |
| 5,345,281 | 9/1994 | Taboda et al. . |
| 5,382,989 | 1/1995 | Uomori et al. . |
| 5,777,718 | 7/1998 | Kohayakawa ........................... 351/211 |

FOREIGN PATENT DOCUMENTS

| | | |
|---|---|---|
| 0 589 857 A1 | 3/1994 | European Pat. Off. . |

OTHER PUBLICATIONS

Koch, et al., "The Corneal EyeSys System: Accuracy Analysis and Reproducibility of First–Generation Prototype", *Refractive & Corneal Surgery*, 5:424–429 (Nov./Dec. 1989).
Bibby, et al., "Corneal Topography—Its Measurement Description Application", Reprinted from Contact Lens Forum (Nov./Dec. 1976–Jan. 1977).
Bogan, et al., "Classification of Normal Corneal Topography Based On Computer–Assisted Videokeratopgraphy", *Archive of Ophthalmology*, 108:945–949 (Jul. 1990).
Rowsey, et al., "Corneal Topography, Corneascope", *Archive of Ophthalmology*, 99:1093–1100 (Jun. 1981).

(List continued on next page.)

*Primary Examiner*—George Manuel
*Attorney, Agent, or Firm*—Knobbe, Martens, Olson & Bear, LLP

[57] ABSTRACT

The invention relates to the art of corneal topography. More specifically, the invention provides many methods and apparatuses for advancing the ease and accuracy of corneal topography. In addition to a front-view camera, one embodiment provides a side (temporal) view camera for viewing the cornea or other reflective surface. The side-view camera may capture a true image of the cornea as well as a reflected placido pattern. The information contained in these images provides capability to automatically find the apex, location of the limbus, vertical profile and curvature out to the limbus. These abilities lead to improved methods for autocalibration and autopositioning as well as other advantages in the field of corneal mapping.

35 Claims, 5 Drawing Sheets

OTHER PUBLICATIONS

Rowsey, et al. "Prospective Evaluation of Radial Keratotomy, Photokeratorscope Corneal Topography", *Ophthalmology*, 95(3):332–334 (Mar. 1988).

Henslee, et al., "New Corneal Shapes In Keratorefractive Surgery", *Opthalmology*, 90(3):245–250 (Mar. 1983).

Gormley, et al., "Corneal Modeling", *Cornea*, 7(1):30–35 (1988).

"Holographic Process Offers Best Potential for Real–time Modeling/Corneal Imaging", *Oscular Surgery News*, 6(4):16 & 18 (Feb. 15, 1988).

"Three–Dimensional Ultrasonic Imaging of the Cornea: A Proposed Technique Would Generate Pictures of Curved Surfaces", NASA Tech. Briefs. NASA's Jet Propulsion Laboratory, Pasadena, CA, p. 99 (Sep. 1988).

"Real–Time Keratometer" Nasa Tech. Briefs. NASA's Jet Propulsion Laboratory, Pasadena, CA, pp. 55–56 (Mar. 1988).

Villasenor, et al., "Corneal Topography and Refractive Surgery", *Cornea*, 2:323–331 (1983).

Doss, et al., "Method for Calculation of Corneal Profile and Power Distribution", submitted to the Archives of Ophthalmology, pp. 1–14 & four pps. drawings (Dec. 1978).

Cotran, et al., "An Adaptation of the Topcon Slit Lamp for Photokeratoscopy", *CLAD Journal*, 13(5):277–279 (Sep. 1987).

Klyce, Stephen, "Corneal Topography Graphically Rendered by New System", *Ocular Surgery News*, pp. 28–29 (Apr. 1, 1987).

Klyce, Stephen D., "Computer–Assisted Corneal Topography", *Investigative Ophthalmology & Visual Science*, 13(12):1426–1435 (Dec. 1984).

Maguire, et al., "Graphic Presentation of Computer–Analyzed Keratoscope Photographs", *Arch. Ophthalmol.*, vol. 105, pp. 223–230 (Feb. 1987).

KM–1000 Basic Principle. "How the KM 1000 Measures the Curvature of the Cornea" (a technical description of the sun optical keratoscope principle).

Clinical Information provided by the Wessley Jessen Co. introducing the IDI corneascope and comparator.

Brochure: "Photo Kerascope Attachment for the Model SL 6E Photo Slit Lamp".

Brochure: "The Leading Edge in Eye Care", Computer Graphics World, (Mar. 1987).

Brochure: "Corneascope", Kera Corporation.

The University of Houston–University Park Subgrant Under the Coordinating Board, Texas University & College System, Subgrantor–Technitex, Inc. *Development of the Photo–Keratographs*, (Aug. 1, 1986 –Jan. 31, 1987).

MULTI-CAMERA CORNEAL ANALYSIS SYSTEM

This is a continuation of application Ser. No. 08/638,875 filed Apr. 25, 1996 now U.S. Pat. No. 5,847,804 which is a file wrapper continuation of Ser. No. 08/330,979 filed Oct. 28, 1994, now abandoned.

1.0 BACKGROUND OF THE INVENTION

1.2 Glossary

Apex: The specification may refer to the "apex of the eye" or "apex of the cornea." Referring to a cross section of an eye in FIG. 1, Apex 101 is the outermost point of the cornea.

Reflecting surface: The specification may refer to a "reflecting surface." It is intended that the term indicate any surface of a unit under test that is suitable for reflecting light (visible or otherwise), such as a ball bearing, marble, or human cornea.

Horizontal Meridian: The horizontal meridian is the profile of the cornea along a line containing the apex and is horizontal with respect to the imaging camera.

Vertical Meridian: The vertical meridian is the profile of the cornea along a line containing the apex and is vertical with respect to the imaging camera.

Z-axis: Generally, the Z-axis refers to an axis in parallel with the optical axis.

Unit Under Test: The "unit under test" refers to a reflecting surface under examination by the topography system. A "unit under test" may be any reflecting surface such as an eye, calibration ball, ball bearing etc.

Keratometer: An instrument for determining the curvature shape of the corneal surface which generally uses a placido or other illuminated target that is centered around the patient's line of sight. The reflection of a placido or other illuminated target by the patient's cornea or by the tear film on the anterior surface of the cornea is subsequently analyzed to determine the surface contour of the eye.

1.1 The History And Background Of Corneal Modeling

A number of forms of eye surgery involve a consideration of corneal surface topography. In radial keratotomy, for example, a number of cuts are made into the cornea in order to change its curvature and correct refractive power so that images focus closer to the retina.

While ophthalmic surgery is often successfully performed, the results obtained have been subject to variation occasioned by the particular operating "style" of the individual surgeon which dictates the number, location and depth of incision. Elements of subjective judgment are paramount. It would be useful to provide a device that could assist the surgeon in more quantitatively assessing pre-operative and post-operative corneal contours.

The present system relates to improvements in the art of photokeratometry and more particularly to the use of multiple camera view in combination with digital image processing techniques to ascertain the radius of curvature, refractive power, vertical profile of the cornea, and location of the apex.

An initial development in keratometry came from Gullstrand in 1896. Gullstrand disclosed the foundation for the current technology but his apparatus had no provision to compensate for aberrations in the optical system other than limiting the photographic coverage of the cornea to a 4 mm area. As a result, multiple exposures and calculations were necessary to map the corneal surface.

Much of the modern technique was developed by Amsler in 1930 and embodied in his "Photo-Keratoscope" which also required measurement and calculation as a separate step to derive the corneal shape data.

A standard instrument which is in common use for central optical zone shape measurement is the Bausch and Lomb Keratometer. Several companies offer similar devices with similar principles of operation. In these devices a single Mire image is projected on a small central portion of the anterior surface of the cornea usually 3 mm in diameter. The user is required to operate several controls to bring the optically split Mire images reflected from the cornea simultaneously into focus and alignment. In addition, the operator manually records the data obtained at two perpendicular axes. Other instruments are also available, such as the Haag-Streit Javal Schiotz device which measures only one axis at a time, but is slightly easier to use and tends to be more accurate in practice than the Bausch and Lomb system. In addition there exists a photographic system made by International Diagnostic Instrument Limited under the trademark "CORNEASCOPE" (and a similar system made by Nidek in Japan), as well as autokeratometers by several manufacturers. The CORNEASCOPE produces instant photographs of the reflection of a placido disc and requires a second instrument separate from the camera assembly to analyze the data. This system is fairly accurate, but expensive and tedious to use. The autokeratometers all are believed to be limited to a single zone of approximately 3 mm diameter and, in cases where the magnitude of the astigmatism is low, are inaccurate in their assessment of axes of astigmatism. Also available are three computer-direct systems which use conventional image analysis algorithms in conjunction with a mini-computer. These are the Corneal Modeling System (CMS) introduce in 1987 by Computed Anatomy, Inc. of New York, N.Y. and the ECT-100. introduced into the market by Visioptic of Houston, Tex. and a system using light emitting diodes disposed in concentric rings built by Zeiss of Germany. The placido disc-photo technique is regarded by some as superior to the Bausch and Lomb Keratometer because of the much greater amount of corneal surface analyzed form the placido reflection as opposed to the MIRES of the Keratometer.

A number of patents have been issued that relate to keratometers. U.S. Pat. No. 3,797,921 proposes the use of a camera to record the placido reflection from a patients eye. From this photograph, the radius of surface curvature of the cornea is determined at several points and calculated using a complex computer system. The use of a ground glass focusing screen with the small aperture of the optical system and large linear magnification makes use difficult and requires a darkened room for operation.

U.S. Pat. No. 4,440,477 proposes a method and device for measuring the corneal surface, comprising a slit lamp for illuminating the corneal surface, a camera for recording the reflection from the corneal surface, and a processor to calculate the image distance and the radius of curvature of the eye. The operation of the processor evidently is not detailed in U.S. Pat No. 4,440,477.

A more recent entry into the market is the "Corneal Modeling System" manufactured by Computed Anatomy Incorporated of New York which uses a light cone placido target in conjunction with a "frame grabber" to digitize and store for conventional image analysis the pictorial data. The placido is in cylindrical form and illuminated from one end.

This cylindrical placido maintains a small aperture optical system creating a large depth of field of focus of the imaging system and, consequently, requires a sophisticated focus determining apparatus to assure accurate and reproducible image evaluation. This system is said to produce corneal thickness data using a scanning laser, as well as the surface contour, but is very expensive and does not readily lend itself to clinical applications which are increasingly cost driven.

The prior art systems generally rely on a front view of the cornea to provide all the expected data. In many respects, this limitation causes significant potential for error or impracticality. The current invention addresses many of the suggested problems by providing a side (temporal) view of the cornea in addition to the traditional front view.

1.3 Problems In The Prior Art

Most current placido based systems cannot provide a three space location of the apex because front-view-only systems operate using a 2-D virtual image. While using a 2-D virtual image, it may be impossible to determine the true Z-axis location of the apex and therefore a three space location of the apex may not be found. While certain laser aided systems have claimed some success in finding the apex, the process is believed to be simpler and faster using the placido based multi-camera system proposed by the current invention.

As with apex location, most current placido based systems technology apparently cannot provide true topography data because of the limitations of the front-view virtual image. However, like the apex situation, the invention addresses this problem by providing a side-view real image in which the true topography can found.

Another limitation in the prior art is the general inability to accurately profile the cornea. A front-view-only system suffers this limitation because there may be no way to accurately locate even a single point on the Z axis. The multi-camera system of the current invention addresses this limitation because a side-view camera is able to profile the Z axis.

In addition to the other limitations discussed, the front-view-only systems in the prior art may cause severe errors because geometrical phenomenon can result in an identical data collection for more than one eye shape. The current invention circumvents this problem by providing a second view to act as a checking mechanism.

Furthermore, the front-view-only systems of the prior art are difficult to use in that they inherently rely on the subjective skill of the operator for accurately positioning the equipment with respect to the eye. For even the most experienced operators, this manual positioning factor can cause serious repeatability problems. The current invention is not as susceptible to these problems because the ability to locate the apex allows a system design whereby the system may auto-calibrate and auto-position. Furthermore, prior art systems can be slow to calibrate and position. Therefore drying of the tear film may result and cause patient discomfort and distorted reflected data.

Lastly, the geometric constraints of single-view placido based systems can make it difficult or impossible to collect data as far out as the limbus. The current invention addresses this problem by using the side view to retrieve the data.

2.0 SUMMARY OF THE INVENTION

As discussed above, prior art corneal topography generally has attempted to assess the surface of the cornea using only a front view of the eye (generally along the optical axis). The invention seeks to improve upon the prior art by assessing corneal topography with a multi-camera corneal analysis system. Generally, this multi-camera system assesses topography in light of a front view as well as a side view that is substantially orthogonal to the front view. Either alone, or in combination with front-view data, side-view data can be used to achieve several beneficial results discussed herein.

In one embodiment, the invention includes a multi-camera corneal analysis system. The invention specifies the addition of a side-view camera subsystem 702. The side-view camera subsystem provides for capture of a corneal image from a vantage point substantially orthogonal to the standard front-view camera. The camera subsystem includes the necessary and conventional circuitry for digitizing a captured image. This particular embodiment envisions that the side-view camera will be rigidly affixed relative to the front-view camera. Of course, given its position, the side-view camera has an optical axis that is substantially orthogonal (75–105 degrees) to the optical axis of the front-view camera. The described embodiment also envisions a subsystem 407 to analyze the digitized images and generate an error signal. The contemplated error signal is defined by the locational displacement of the apex from either (1) a desired position for the apex or (2) a point on a predefined coordinate system. Of course, the coordinate system may be easily defined by any one optical axis or the intersection of any two. Lastly, the described embodiment envisions the visual display of periodically updated information.

Another embodiment of the invention includes a third camera (second side-view camera) mounted opposite the first side-view camera and substantially orthogonal to the front-view camera. The optical axes of the side view cameras may coincide, cross or exist in parallel.

Yet another embodiment of the invention uses a side view camera to receive images reflected off a reflecting surface. The source of the image may be a placido. One skilled in the art will recognize the many embodiments that may be created by combining the advantages of a side-view camera with the many other elements of the a corneal analysis system. For example, given the apex-finding capabilities of the multi-camera system, an embodiment may be constructed to determine the desired location of the apex and even automatically adjust the cameras to align with the apex.

Several methods are contemplated to take advantage of the usefulness of the side-view camera. One of the contemplated methods includes steps for finding the apex of a reflecting surface. In brief, an image is captured by a side view camera and the apex is located at the leading edge of the cornea's vertical profile. Furthermore, consistent with the envisioned system, the method may specify that an error signal is generated to represent the difference between an actual apex location and a desired apex location.

The invention also includes a method of finding radius of curvature using a side view camera. Essentially, the system of the invention is used to gather a table of data for reflecting surfaces having known radii of curvature, e.g., balls. Specifically, the table should contain data representing known radii of curvature versus measured distances between specified locations on a pattern reflected off the surfaces (balls). After the table is constructed, the same pattern-location to pattern-location measurements are made for a unit under test. The radius of curvature are then found by interpolation with the know radii and measured distances.

Another aspect of the invention is a method of locating a point on a limbus. The side-view camera is used to capture an image of the cornea. The limbus is then found as the transition between a homogeneous white region and a non-homogeneous region. Of course, this result may be achieved using digitized images and detecting the transition between energy regions.

Yet another embodiment of the current invention is a method of finding a profile of a reflecting surface. An image is captured from a side view camera and digitized. Once digitized, the image may be high-pass filtered. The profile is then found at a high to low energy transition.

3.0 BRIEF DESCRIPTION OF THE DRAWINGS

4.0 DETAILED DESCRIPTION OF THE INVENTION 4.1 A Multi-Camera Apparatus

Figure 3:
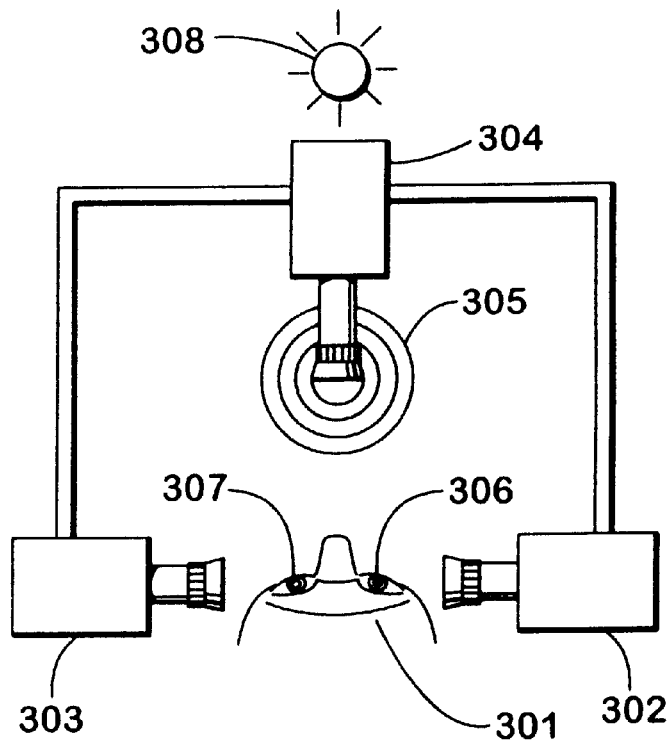
FIG. 3 is a three camera embodiment of the invention.

Referring to FIG. 3, a three camera embodiment of the invention is shown. Front view camera 304 has its optical axis generally aligned with the optical axis of the eye under exam 306 or 307. Of course, at any given time, front view camera 304 may be used for examining either left eye 307 or right eye 306, but not both. Side-view cameras 302 and 303 are each positioned substantially orthogonal to front view camera 304. Left-side-view camera 303 is used only for examining left eye 307 because human facial anatomy (usually a nose) substantially restricts visibility of right eye 306 from the vantage point of left-side-view camera 303. Of course, for the same reason, right-side-view camera 302 is only used for examining right eye 306. In one embodiment, left-side-view camera 303 and right-side-view camera 302 share a common optical axis.

Figure 5:
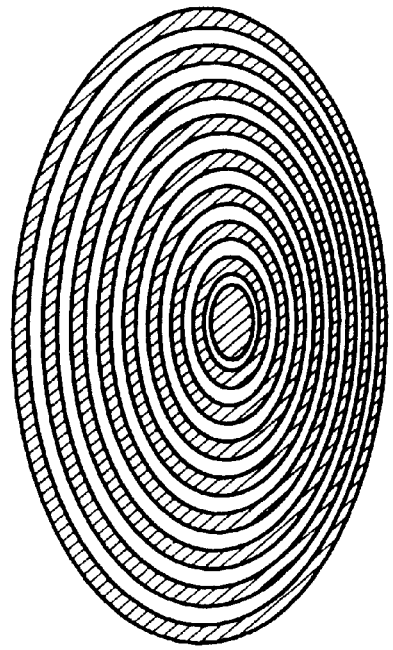
FIG. 5 is a photograph of a processed profile of a sphere.
Figure 6:
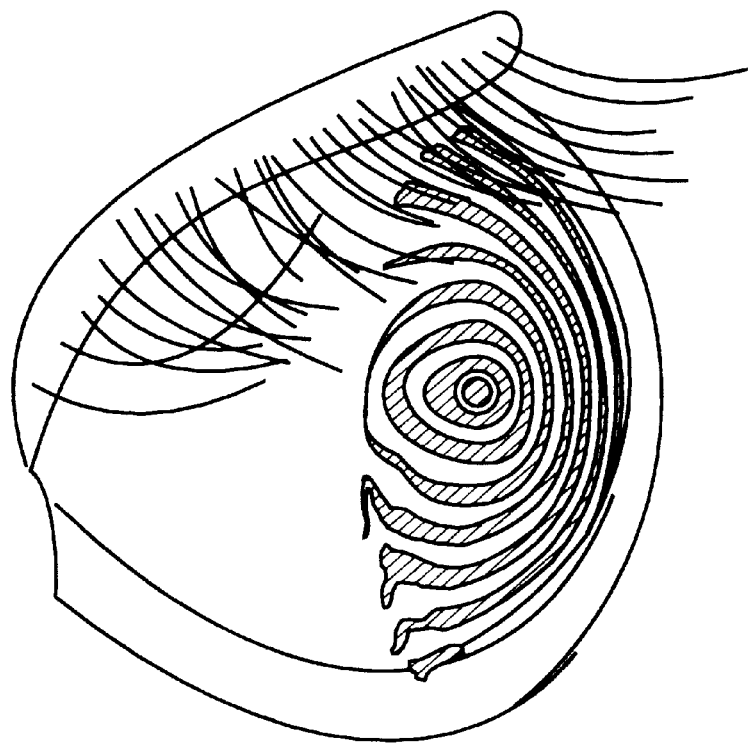
FIG. 6 is a photograph of a processed profile of an optical sphere.

During a typical use of the invention, for example examining a right eye, a person under exam 301 will face placido 305 and generally align the optical axis of right eye 306 with the optical axis of front view camera 304. Light source 308 will cause the pattern from placido 305 to reflect off of right eye 306. The reflected pattern as well as a real image of the right eye 306 may be captured by front-view-camera 304 and right-view-camera 302. The corneal image captured by front-view-camera 304 is well known in the art and therefore not discussed further. However, the image captured by the right-side-view camera is not well known and provides two very useful data sources: (1) a true profile of the cornea; and (2) a view of the reflected placido rings on the temporal hemisphere. An example of this data is shown in photographs labeled as FIG. 5 and FIG. 6. Specifically, a processed interpretation of a side-view image is shown in FIG. 6 (for a human eye) and FIG. 5 (for a sphere). Another typical use of the invention is, for example, examining the left eye 307. In this use, a person under exam 301 will face placido 305 and generally align the optical axis of left eye 307 with the optical axis of front view camera 304. The reflected pattern, real image and true profile of left eye 307 may then be captured by front-view-camera 304 and left-view-camera 303.

It will be apparent to those of ordinary skill having the benefit of this disclosure that the effect of a multi-camera system is to simultaneously achieve two views of a single eye (or cornea): a side view and a front view. It is contemplated that this effect can be achieved with fewer than three cameras. For example, two cameras may be oriented for use with one eye and then re-oriented for use with the other eye. Alternatively, one camera may be adapted with lenses or mirrors so that side and front views may be simultaneously received. Lastly, simultaneous views may be simulated by time sharing one camera with two or more views.

While no specific embodiment is envisioned, the invention also contemplates using a third view taken from the top or bottom vantage point. This third view may lead to even further accuracy in corneal topographic mapping by providing new information as well as verification information.

4.1.1 Orientation of Views

Figure 4:
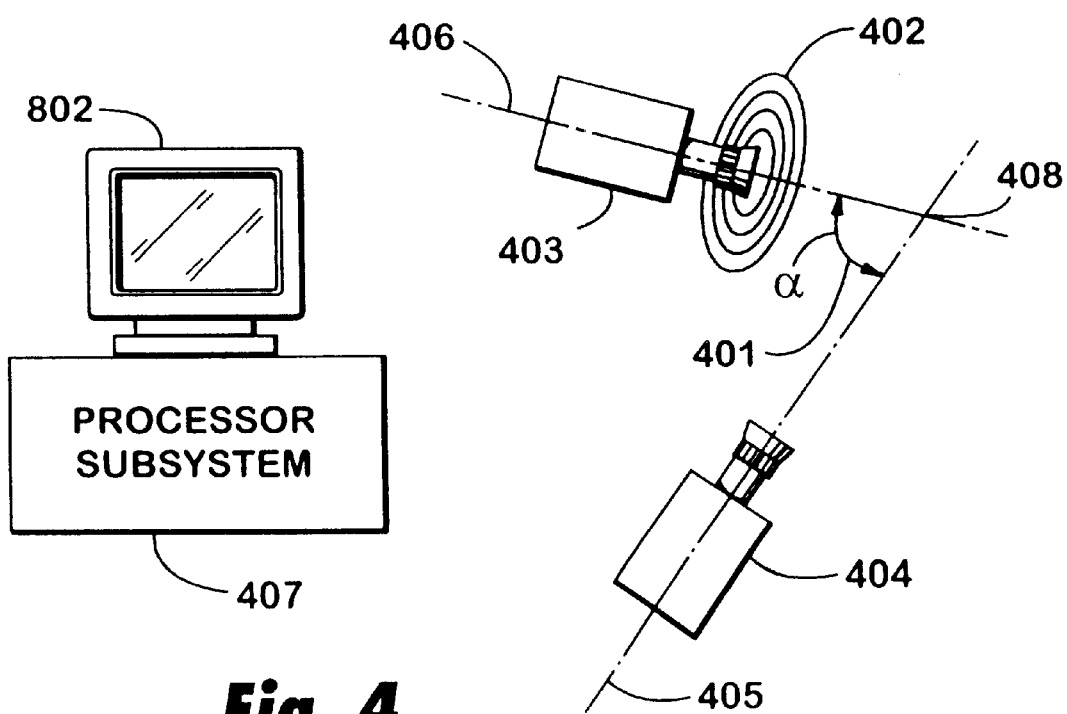
FIG. 4 is a two camera embodiment of the invention.

Referring now to FIG. 4, an abstract view of a multi-camera system is shown. Here, it can be seen that the optical axis 406 of front-view camera 403 is at angle $\alpha$ with the optical axis 405 of side-view camera 404. Any orientation of side-view camera 404 relative to front-view camera 403 may be used as long as the respective optical axes are substantially orthogonal to one and other; a maximum variation of $\alpha$ from 75 degrees to 105 degrees is preferred. However, it has been found that better performance may be achieved for a between 85 degrees and 95 degree. Furthermore, it has also been determined that $\alpha$ is optimum at 90 degrees.

While angle $\alpha$ is restricted as stated above, the relative orientation of side-camera 404 and front-camera 403 may be otherwise altered to maximize the view of the cornea. For example, some patients have facial structures that do not easily accommodate a side view of the cornea. In this instance, the corneal view may be improved by rotating side-view camera 404 about the optical axis of front-view camera 406.

4.1.2 Processor Subsystem

In order to increase efficiency and performance, a processor subsystem 407 is used to perform control and interface functions. Processor subsystem 407 initiates or performs all control functions and digital operations. Specifically, processor subsystem 407 is programmed to perform the functions necessary to receive meaningful data from the multi-camera system. For example, radius of curvature, position of the limbus, auto-calibration and error correction all benefit from computational activity in processor subsystem 407. Of course, the functions of processor subsystem 407 may be distributed across various devices or computers.

Figure 8:
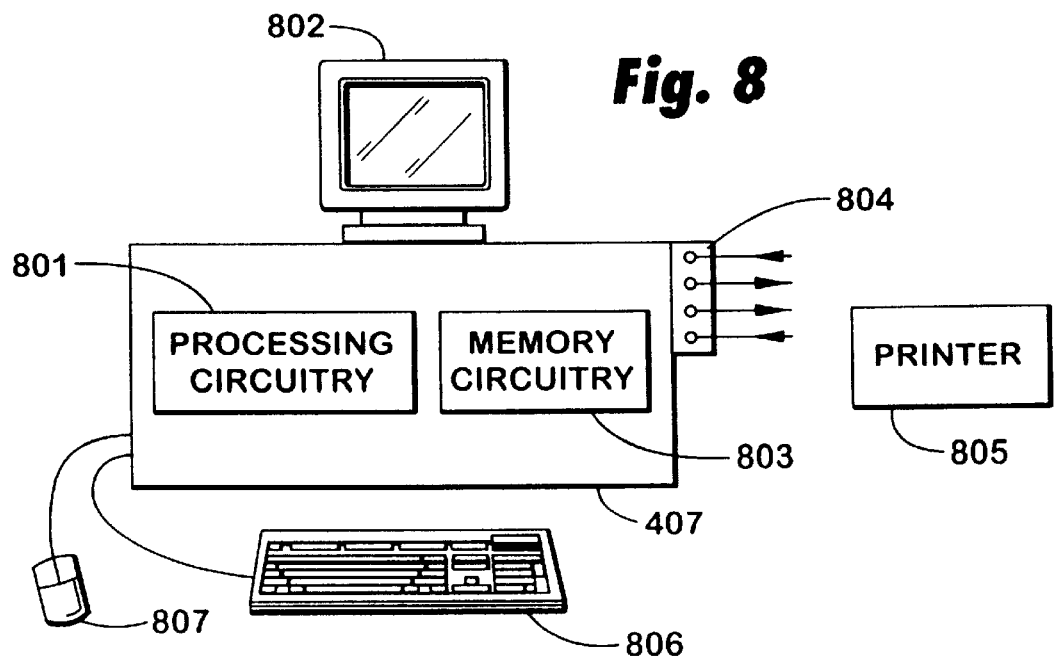
FIG. 8 is an embodiment of a processor subsystem.

Referring to FIG. 8, the main elements of processor subsystem 407 are shown. Fundamentally, processor subsystem 407 may include processing circuity 801, memory circuitry 803 and port 804. Processing circuitry 801 and memory circuitry 803 are used for receiving, executing and implementing computer instructions. The processing circuitry 801 typically comprises a PC microprocessor system, although any combination of single or multiple microprocessors or instruction fetch and execution circuitry will suffice. The memory circuitry 803 is contemplated as a conventional PC combination of DRAM and SRAM circuits. Of course the invention may be implemented using any electronic, magnetic or other memory option. Port 804 is the gateway between processor subsystem 407 and the outside world. The processor subsystem 407 may also include interface elements such as monitor 802, keyboard 806, mouse 807 and printer 805. Any conventional computer may be adapted for use as processor subsystem 407.

4.1.3 Camera Subsystem and Camera Assembly

Figure 7:
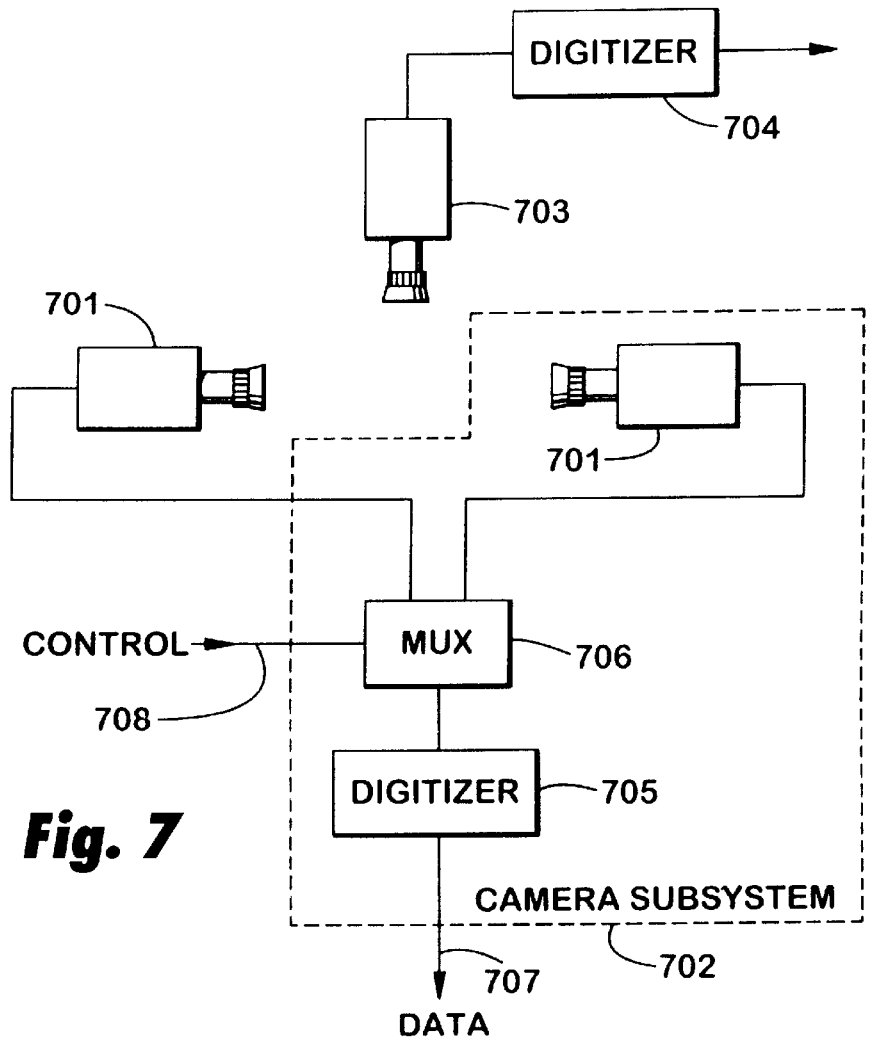
FIG. 7 is a three camera embodiment of the invention.

The invention contemplates the use of digital signal processing. Therefore, it is appropriate to represent the video images digitally. To fulfill this function, the system may employ a camera subsystem contained in an overall camera assembly. Referring to FIG. 7, a camera assembly having three camera subsystems is shown. In function, a camera subsystem 702 receives an image and then represents that image in digital form. The digitized image is then passed on to processor subsystem 407 via data line 707. A camera subsystem 702 may contain the following: (1) a camera 701 or other device suited to receive images; and 2) a digitizer 705 or other means for creating a digital representation of the received images, e.g. a CCD or analog-to-frame-grabber arrangement. A camera subsystem 702 may also contain a multiplexer. The multiplexer functions to select one of two side view cameras 701 in a three camera embodiment of the multi-camera system. The multiplexer is controlled by a processor subsystem 407 via control line 708. It is noteworthy that any part or all of a camera subsystem 702 may also be part of a processor subsystem 407.

4.1.4 Other Embodiments

One skilled in the art, will, of course, recognize that this invention is not restricted by the specific embodiment presented here. For example, a pattern may be reflected off the eye by using a placido or any other reasonable means such as L.E.D.s or fiber optics. Furthermore, the invention is not strictly limited to the examination of a human eye. The invention may also be used to obtain topography information about any eye or similarly shaped object such as a ball bearing, calibration sphere, contact lens or artificial tears. Moreover, images may be captured by means other than cameras. For example any CCD array or analog camera type device may be used.

4.2 Auto-Positioning; Aligning the Apex

Figure 1:
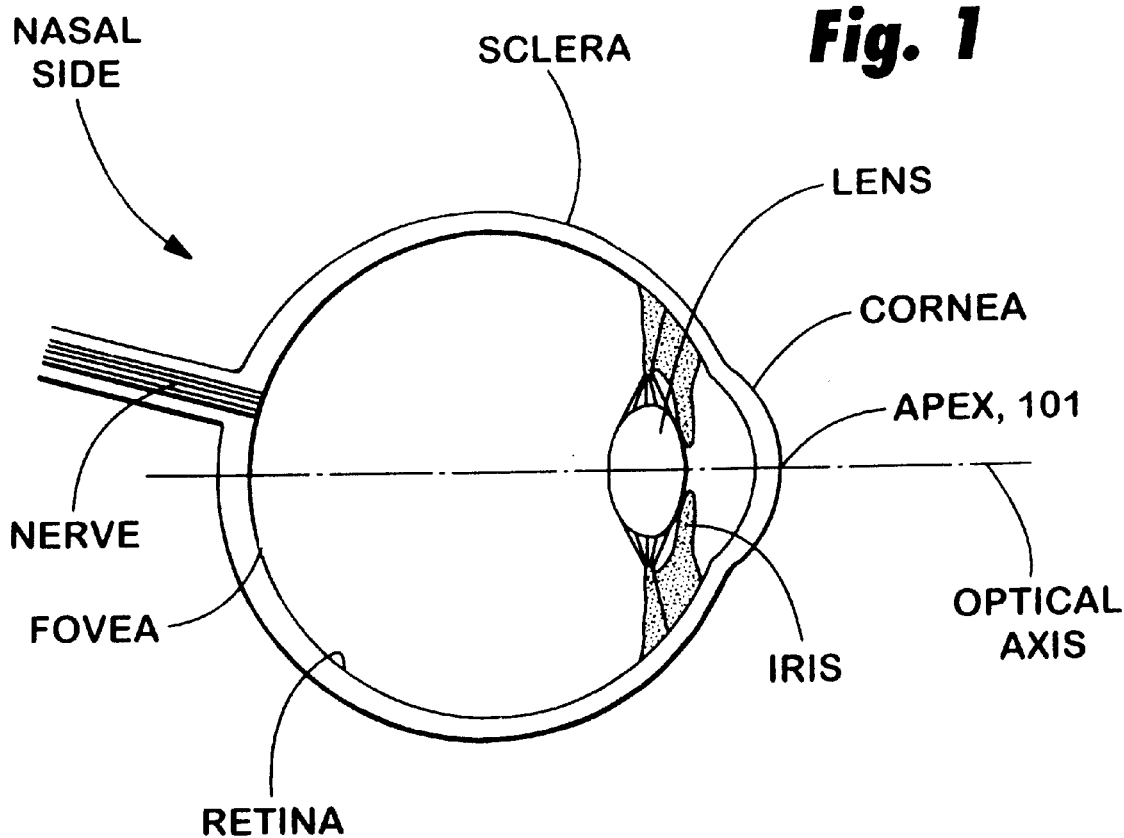
FIG. 1 is profile of a human eye.
Figure 2:
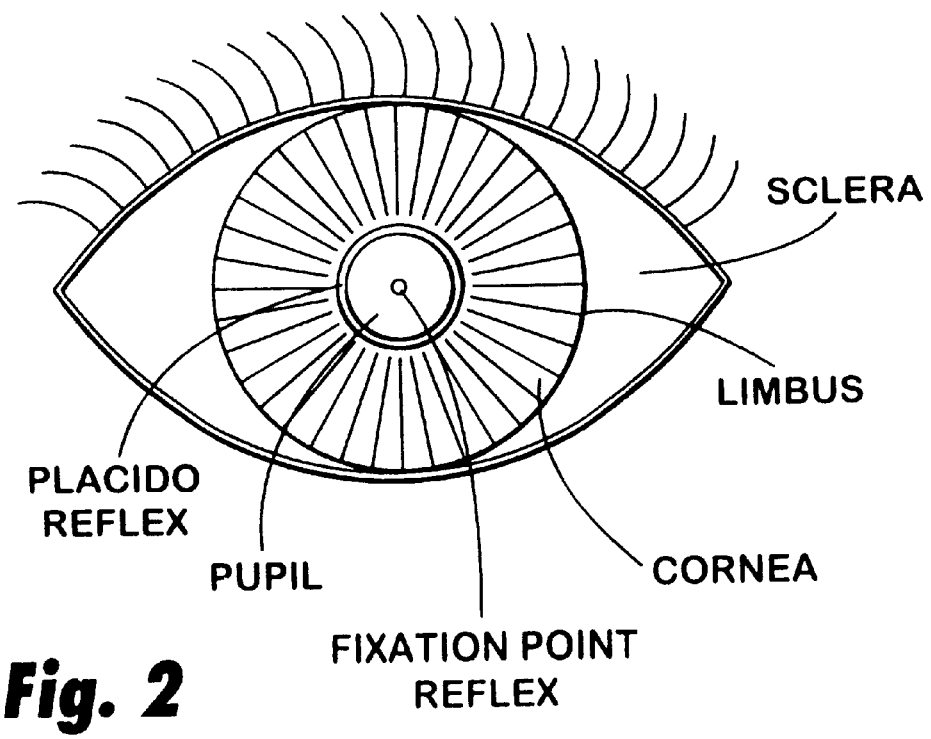
FIG. 2 is a front-view of a human eye.

In prior art corneal topography systems, the apex of the eye is aligned with the optical axis of the camera through various conventional techniques. Generally, none of these techniques can provide a precise alignment because, when only a front-view camera is employed, the system must estimate the Z-axis location of the apex. The current invention addresses this problem by precisely locating the apex via a side-view camera. Specifically, as previously discussed, a side-view camera according to the invention can capture an image of the true corneal profile, e.g. FIG. 1 shows a drawing of a corneal profile and FIG. 6 shows an actual photo of the same. Given the side-view corneal image, the apex is identified as the leading edge of the profile. For example, apex 101 is found at the leading edge in the corneal profile of FIG. 1.

Applying this concept to the disclosed embodiments, side-view camera 404 captures an image of the corneal profile. The image is digitized by a digitizer in the camera 404's subsystem. The apex, or leading edge, is then located according to the procedures in the supplemental disclosure to this specification. More particularly, processor subsystem 407 receives digitized images of both front and side views. Using the front view, processor subsystem 407 may determine the expected location of the apex in three dimensions (X, Y and Z) and the actual location in 2 dimensions (X and Y). As indicated above, using the side view, processor subsystem 407 may determine the actual Z-axis location of the apex. Having both the expected and actual location, processor subsystem 407 may generate an error signal indicating or representing the locational difference between the true and expected locations of the apex. Given the foregoing information, processor subsystem 407 may also generate a signal indicating or representing the position of the apex relative to an X, Y, Z coordinate system such as the system defined by point 408 and the intersection of side-view optical axis 405 with front-view optical axis 406. Of course, all the described activity may be visually represented on monitor 802 or by printing of printer 805.

4.2.1 Closed-Loop Positioning

Figure 9:
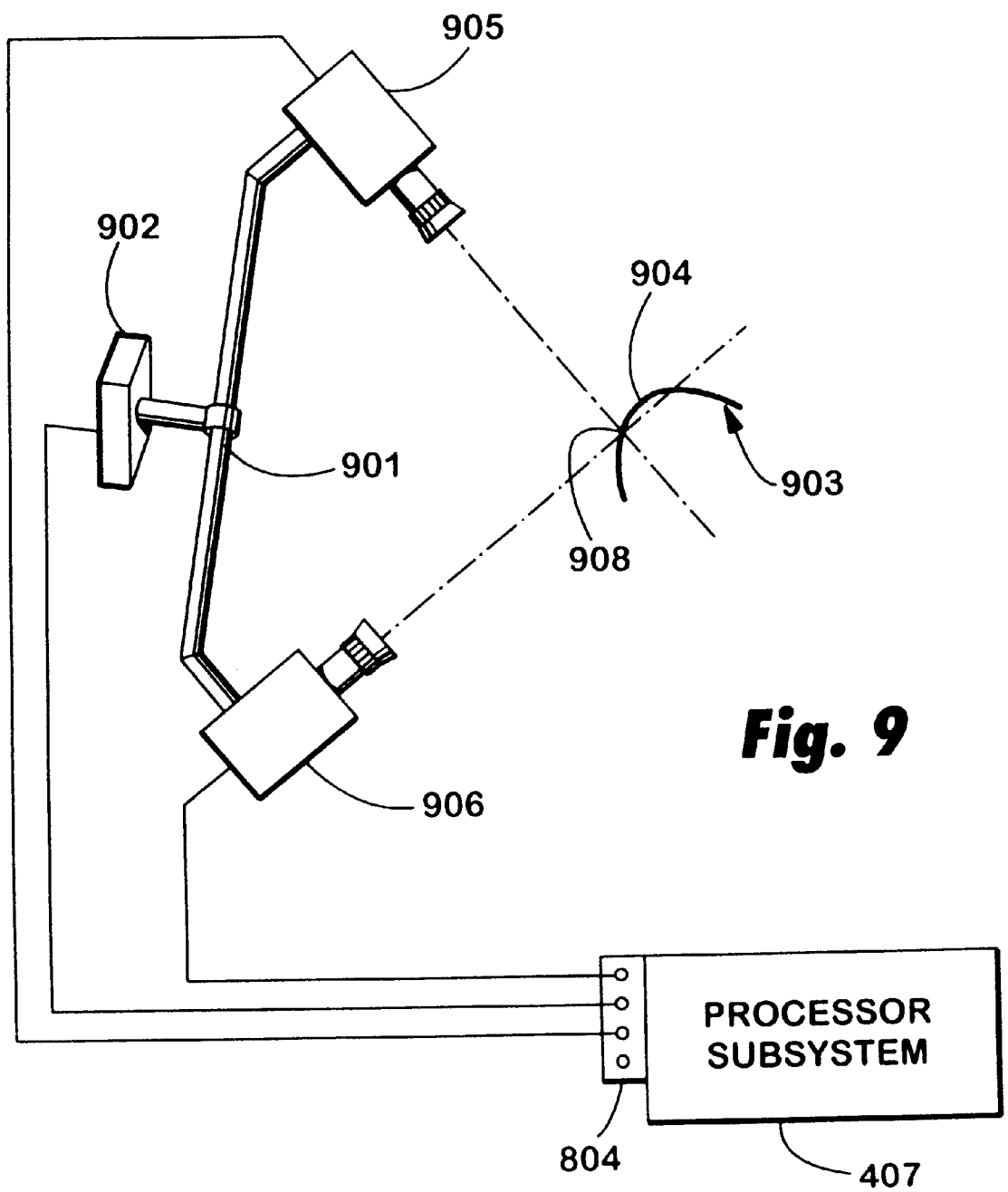
FIG. 9 is a two camera embodiment of the invention.

The invention contemplates using the described error signal to physically change the position of the camera assembly so that the apex of the eye (or other unit under test) is aligned with the optical axis of the front-view camera. This position may be changed either manually or automatically. Referring to FIG. 9, front-view camera 905 is connected to side-view camera 906 by rigid connection 901. Furthermore, mechanical controller 902 has a moving arm that is firmly coupled to rigid connection 901. This overall assembly allows mechanical controller 902 to move the camera assembly without changing the relative to positioning between front-view camera 905 and side view camera 906.

In operation, front-view and side-view images are captured and digitized. The digitized images are processed in processor subsystem 407 and an error signal is generated representing the actual position of apex 904 relative to the desired position for the apex. The desired position is typically at origin 905 which is the intersection of the optical axis. However, the desired position may be elsewhere, e.g. the system may simply seek to align a single optical axis with the apex.

The error signal is used, either directly or indirectly, to control the actuation of mechanical controller 901. Upon receiving an actuation signal, mechanical controller 901 will alter the position of the camera assembly. For higher accuracy this process may be iterated until the apex is positioned precisely as desired. Of course, the error signal may be used in other ways. For example, the error signal may be used for the following purposes: 1) to correct calculations (such as radius of curvature) made on an eye (or other unit under test) that is not ideally positioned relative to the cameras; or 2) to generate a graphical representation of the error to display on a monitor or printer. These uses of the error signal are further discussed in the context of specific embodiments in appendixes 1 and 2.

4.3 Finding Curvature Using The Side-View Camera

As mentioned earlier, a side-view image allows calculation of radius of curvature, along the horizontal, up to the limbus. The calculation is facilitated by the side-view camera's capture of the reflected placido pattern (typically rings). Furthermore, curvature is ultimately determined by collecting data from an eye (or other unit under test) and interpolating the collected data with similar data taken from objects having known radii of curvature.

Specifically, the process begins by collecting a reference set of reflecting surfaces (calibration balls) having known radii of curvature. The reference set should include enough balls of varying size to create a scale large enough and granular enough so that accurate interpolation is possible against data taken from the intended class of units under test. Each all may be placed under test, for example by (i) reflecting rings off the ball, (ii) capturing an image of the ball with a side view camera, and (iii) measuring the distance from the apex to the edges of all the rings (or measuring the distance between adjoining ring edges). The measured distances may be cataloged with the corresponding radius of curvature of the examined ball. Once all the balls are examined, a full table may be constructed revealing radius of curvature versus distances (either apex to various edge or edge to edge). Finally, when an eye (or other unknown unit under test) is examined, the apex to edges (or edge to edge) distances may again be measured and the radius of curvature may be calculated by linear or other interpolation with the collected data.

4.4 Locating The Limbus

The multi-camera system may also be used to find the location of the limbus in three space (X,Y,Z). The Z-axis position of the limbus is obtained with the side-view camera. Once a side view image is obtained, a point on the limbus edge can be found by locating the transition from homogeneous white region to non-homogeneous region on any horizontal line in the side view corneal image. All the relevant points along the limbus may be located in this same manner.

A real image from the front camera may then be used to locate the limbus' Y-axis and X-axis position. Once again, the limbus is located by finding the transition from homogeneous white region to non-homogeneous region. Through this process, the limbus if finally located in three space.

It is noteworthy that locating the limbus may be conveniently accomplished by digitizing the captured images. Since the limbus will always embody a transition from homogeneous white region to non-homogeneous region, the limbus is easily located through various image processing techniques. For example, an intensity profile of the image will show white regions as low energy regions and reflected ring regions as high energy regions. Therefore the location of the limbus will correspond to the transition from a high energy to a low energy region.

4.5 Finding A Profile

A corneal profile may be located by using the multi-camera system. Specifically, a profile along the horizontal meridian is found by using a virtual image (the reflected pattern) obtained through the side-view camera. The virtual image is digitized (to create an intensity profile) and then high pass filtered. The profile is then located at the near-camera boundary between a high energy region and a low energy region. This process is described in detail in appendix 1.

4.6 Additional Disclosure

As supplemental disclosure, the following has been provided: 1) Appendix 1 containing a draft paper written by an inventor (Dr. Sarver); and 2) Appendix 2 containing inventor's documentation.

What is claimed:

1. An apparatus for measuring a radius of curvature of a reflecting surface, said reflecting surface having an apex, comprising:
   (a) means for reflecting an image on said reflecting surface;
   (b) a front-view camera subsystem having an optical axis and a field of view that includes said reflecting surface, said front-view camera subsystem including means for generating a digitized representation of said image;
   (c) a processor subsystem programmed to process said digitized representation to produce an estimate of said radius of curvature;
   (d) a first side-view camera subsystem:
      (1) having a field of view that includes said reflecting surface,
      (2) including means for generating a digitized representation of said image,
      (3) having an optical axis that is substantially orthogonal to the optical axis of said front-view camera subsystem;
   (e) the respective optical axes of said front-view camera subsystem and said first side view camera subsystem collectively defining a coordinate system having an origin;
   (f) said first side-view camera subsystem and said front-view camera subsystem being referred to collectively as a camera assembly; and
   (g) a processor subsystem programmed to analyze said digitized video representations generated by said front-view camera subsystem and said first side-view camera subsystem and to generate an error signal representing a displacement of said apex relative to said origin.

2. The apparatus of claim 1, wherein said origin of the coordinate system is defined by the intersection of said optical axes.

3. The apparatus of claim 1, wherein said reflecting surface is a human cornea.

4. The invention of claim 1, wherein said reflecting surface is a contact lens.

5. The apparatus of claim 1 wherein said side-view camera subinvention is rigidly positioned relative to said front-view camera subsystem.

6. The apparatus of claim 1, further comprising a closed-loop electromechanical positioning system for positioning said camera assembly so that the origin of said coordinate system is at the apex of said reflecting surface.

7. The apparatus of claim 6, wherein said positioning system is automatic.

8. The apparatus of claim 1, wherein said processor subsystem is programmed to generate a positional signal representative of the position of said apex relative to said coordinate system.

9. The apparatus of claim 8, further comprising a visual display of said positional signal.

10. The apparatus of claim 9, wherein said visual display is periodically updated.

11. The apparatus of claim 1, wherein said camera assembly further comprises a second side-view camera subsystem rigidly positioned relative to said front-view camera subsystem and said first side-view camera subsystem.

12. The apparatus of claim 11, wherein said second side-view camera has an optical axis that lies in the plane that contains the optical axis of said first side-view camera.

13. The apparatus of claim 12, wherein the optical axis of said second side-view camera is parallel to the optical axis of the first side-view camera.

14. The apparatus of claim 1, wherein said processor subsystem is programmed to process said error signal to generate a correction to said estimate of the radius of curvature.

15. The apparatus of claim 1, wherein the displacement of said apex that is represented by said error signal comprises a displacement along the optical axis of said front-view camera subsystem.

16. An apparatus for analyzing a reflecting surface having an apex comprising:
   (a) means for reflecting an image off said reflecting surface;
   (b) a front-view camera for generating a front view signal representing said image;
   (c) a side-view camera for generating a side-view signal representing said image;
   (d) a processor subsystem for receiving and processing said front-view image and said side-view image wherein said processor subsystem evaluates said side-view image and detects the apex of the curved image by detecting a leading edge and wherein the processor sub-system uses the apex location information to generate a signal indicative of the displacement of the apex from a desired position.

17. A method of finding the apex of a reflecting surface in a multi-camera corneal analysis system having a camera assembly including a side-view camera and a front-view camera comprising:

(a) using said side view camera to capture an image of said reflecting surface;

(b) determining an actual apex location by detecting a leading edge with the side-view camera;

(c) determining a desired apex location; and (d) generating an error signal representing a difference between said actual location and said desired location.

18. The method of claim 17 further comprising:

(a) determining a desired apex location; and (b) generating an error signal representing a difference between said actual location and said desired location.

19. The method of claim 17, further comprising displaying a representation of said error signal.

20. The method of claim 17, further comprising printing a representation of said error signal.

21. The method of claim 17, further comprising using said error signal to drive an electromechanical positioning system for positioning said camera assembly so that said apex is located at said desired location.

22. The method of claim 17, further comprising using said error signal to correct a radius of curvature measurement of a reflecting surface.

23. A method of locating a point on a limbus comprising:

(a) using a side-view camera to capture an image of an eye; and (b) locating a point on a horizontal line where there is a transition from a homogeneous white region to a non-homogeneous region.

24. The method of claim 23 wherein the locating step comprises:

(a) generating a digital representation of said image, said digital representation having low energy signals and high energy signals; and (b) detecting a location of a point on the limbus by locating a transition between said high energy signals and said low energy signals.

25. A method of finding a point on a profile of a reflecting surface comprising:

(a) using a side-view camera to capture an image of a reflecting surface;

(b) generating a digital representation of said image, said digital representation comprising data;

(c) filtering, through a high-pass filter, at least a portion of said data to generate a filtered signal comprising high energy signals and low energy signals;

(d) detecting, in said filtered signal, a transition between said high energy signals and said low energy signals.

26. A method of automatically calibrating a multi-camera corneal analysis system having a front-view camera and a side-view camera, comprising:

(a) using said side-view camera to detect an actual Z-axis location of an apex with respect to a desired location of said apex;

(b) using said front-view camera to detect an actual X-axis and Y- axis location of an apex with respect to said desired location of said apex, the combination of said side-view camera and said front view camera being called said camera assembly;

(c) generating an error signal for each axis, X, Y and Z, said error signals defined by a difference between said actual locations and said desired locations.

27. The method of claim 26, further comprising:

using said error signal to drive an electromechanical positioning system for positioning said camera assembly so that said apex is located at said desired location.

28. An apparatus for analyzing a patient's eye, the apparatus comprising:

a front view camera adapted to be positioned substantially in front of the patient's eye so that the camera can obtain a front view image of the patient's eye;

a side view camera adapted to be positioned to the side of the patient's eye wherein the side view camera is adapted to receive a side view image of the eye; and a processor that receives data representative of the side view image of the eye, wherein the processor is adapted to analyze the data so as to determine the location of the apex of the patient's eye along an axis extending substantially perpendicularly out of the apex and provide a signal representative of the location of the apex of the eye.

29. The apparatus of claim 28, further comprising an illuminated target that produces a reflected image on the patient's eye that can be obtained by the front view and the side view camera.

30. The apparatus of claim 29, wherein the illuminated target produces a placido image.

31. The apparatus of claim 28, wherein the processor determines the position of the apex with respect to a desired position of the apex and provides an error signal indicative thereof.

32. The apparatus of claim 31, wherein the front view camera and the side view camera each define an optical axis that intersect each other and the desired position of the apex is defined relative to the intersection point of the optical axes.

33. The apparatus of claim 32, wherein the optical axes of the two cameras intersect at an angle between 85 and 95 degrees.

34. The apparatus of claim 31, wherein the processor further receives data representative of the front view of the eye and wherein the processor is adapted to use data representative of the front view image to determine the radius of curvature of the patient's eye.

35. The apparatus of claim 34, wherein the processor is adapted to process the error signal to generate a correction to the estimated radius of curvature.

* * * * *